United States Patent [19]

Eudy

[11] 4,282,366

[45] Aug. 4, 1981

[54] ORGANOSILICON QUATERNARY AMMONIUM ANTIMICROBIAL COMPOUNDS

[75] Inventor: William W. Eudy, Cornwall-on-Hudson, N.Y.

[73] Assignee: International Paper Company, New York, N.Y.

[21] Appl. No.: 91,749

[22] Filed: Nov. 6, 1979

[51] Int. Cl.$^3$ .............................................. C07F 7/10
[52] U.S. Cl. .................................... 556/413; 71/67; 424/184; 106/18.32; 8/188
[58] Field of Search ........................................ 556/413

[56] References Cited

U.S. PATENT DOCUMENTS

| | | | |
|---|---|---|---|
| 3,402,191 | 9/1968 | Morehouse | 556/413 |
| 3,471,541 | 10/1969 | Morehouse | 556/413 |
| 3,557,178 | 1/1971 | Gölitz et al. | 260/448.8 |
| 3,560,385 | 2/1971 | Roth | 556/413 UX |
| 3,624,120 | 11/1971 | Yetter | 556/413 |
| 3,658,867 | 4/1972 | Prokai | 556/413 |
| 3,661,963 | 5/1972 | Pepe et al. | 556/413 |
| 3,730,701 | 5/1973 | Isquith et al. | 556/413 UX |
| 3,794,736 | 2/1974 | Abbott et al. | 556/413 UX |
| 3,817,739 | 6/1974 | Abbott et al. | 556/413 UX |
| 3,860,709 | 1/1975 | Abbott et al. | 556/413 |
| 3,865,728 | 2/1975 | Abbott et al. | 556/413 UX |

FOREIGN PATENT DOCUMENTS

2226823 4/1973 Fed. Rep. of Germany .

OTHER PUBLICATIONS

"Applied Microbiology", 24, No. 6, pp. 859-863, (1972).
"Applied Microbiology", 25, No. 2, pp. 253-256, (1973).
"Textile World", p. 80, 1975.
"Dow Corning Antimicrobial Agents", 1972.

*Primary Examiner*—Paul F. Shaver
*Attorney, Agent, or Firm*—Ronald A. Schapira

[57] ABSTRACT

The use as antimicrobial agents of organosilicon quaternary ammonium compounds of the formula:

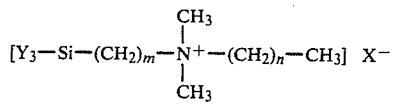

wherein m+n is 16 to 19, m is 1 to 6, and n is 13 to 17 or m+n is 20 to 23, m is 4 to 11 and n is 9 to 17; X is a halogen; and Y is a hydrolyzable radical or hydroxy group.

Substrates, such as cellulose fabrics, can be impregnated with these compounds, so that the growth of disease causing microorganisms in and on the substrates is inhibited.

3 Claims, No Drawings

ORGANOSILICON QUATERNARY AMMONIUM ANTIMICROBIAL COMPOUNDS

BACKGROUND OF THE INVENTION

This invention relates to a method of using certain organosilicon quaternary ammonium halides for treating the surface of a substrate, such as a cellulose fabric, so that the surface is made resistant to the growth of microorganisms. This invention also relates to certain novel organosilicon quaternary ammonium chlorides which demonstrate relatively high levels of antimicrobial activity.

The use of selected organisilicon quaternary ammonium halides for rendering surfaces resistant to the growth of microorganisms is known. See, in this regard, German Offenlegungsschrift No. 2,226,823 and Isquith et al, "Surface-Bonded Antimicrobial Activity of an Organosilicon Quaternary Ammonium Chloride", *Applied Microbiology*, vol. 24, no. 6, pp. 859-863 (1972). In particular, it is known that the hydrolysis products of N-(3-trimethoxysilyl)propyldimethyloctadecylammonium chloride possess significant antimicrobial activity against a broad range of microorganisms while such products are chemically bonded to a variety of surfaces. Because of such antimicrobial activity, N-(3-trimethoxysilyl)propyldimethyloctadecylammonium chloride has been applied to fabrics, such as sheets for hospitals, nursing homes and hotels, in order to aid in the control of disease causing microorganisms on and within the fabrics. See "Blended Sheet Repels Germs, Fungi, Mildew", *Textile World*, p. 80 (November 1975).

SUMMARY OF THE INVENTION

In accordance with this invention, a substrate is treated with an organosilicon quaternary ammonium compound of the formula:

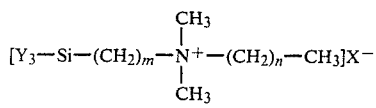
I wherein m+n is 16 to 19, m is 1 to 6 and n is 13 to 17 or m+n is 20 to 23, m is 4 to 11 and n is 9 to 17; X is a halogen; and Y is a hydrolyzable radical or hydroxy group.

The substrate, when treated in accordance with this invention with a compound of formula I, demonstrates a significantly greater resistance to the growth of microorganisms than does the substrate when treated with N-(3-trimethoxysilyl)propyldimethyloctadecylammonium chloride.

Among the organosilicon quaternary ammonium halides of formula I, the chloride compounds of this invention having the following formula are novel:

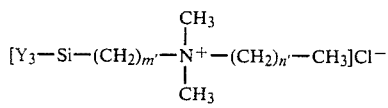
II wherein m'+n' is 16 to 19, m' is 1 or 4 to 6 and n' is 13 to 17 or m'+n' is 20 to 23, m' is 4 to 11 and n' is 9 to 17; and Y is as defined above.

The novel organosilicon quaternary ammonium chlorides of formula II can be used to provide a substrate with a significantly greater resistance to the growth of microbial organisms than is provided by treating the substrate with N-(3-trimethoxysilyl)propyldimethyloctadecylammonium chloride.

DETAILED DESCRIPTION OF THE PREFERRED EMBODIMENT

As used herein, the term "hydrolyzable radical" encompasses conventional chemical groups (Y) on the silyl moiety (Si) of the organosilicon quaternary ammonium compounds of this invention, which will react with water at room temperatures (25° C.) to form hydroxy groups on the silyl moiety of such compounds. Among the hydrolyzable radicals are:

(a) the lower alkoxy groups of 1 to 7 carbon atoms, e.g., methoxy, ethoxy, isopropoxy, butoxy, isobutoxy, beta-ethoxyethoxy, beta-chloroethoxy, gamma-chloropropoxy and cyclohexyloxy;

(b) the aryloxy groups of 6 to 9 carbon atoms, e.g., phenoxy and benzyloxy;

(c) the halogens, such as chlorine, bromine and iodine;

(d) the acyloxy groups of 1 to 10 carbon atoms, e.g., acetoxy, propionoxy and benzoyloxy;

(e) the ketoxime groups, such as the groups of the formula $Z_2C=NO-$ wherein Z is a lower alkyl group of 1 to 7 carbon atoms, e.g., methyl, ethyl and isopropyl, a cycloloweralkyl group of 4 to 7 carbon atoms, e.g., cyclohexyl, or an aryl group of 6 to 9 carbon atoms, e.g., phenyl and benzyl; and (f) the amine groups, such as the groups of the formulas $-NH_2$, $-NZH$ and $-NZ_2$ wherein Z is as defined above.

The preferred hydrolyzable radicals on the compounds of this invention are the lower alkoxy groups, particularly methoxy.

As also used herein, the term "halogen" encompasses fluorine, bromine, chlorine and iodine, unless other expressly stated. The preferred halogen of this invention is chlorine.

Among the preferred organosilicon quaternary ammonium compounds of formula I of this invention are compounds in which each hydrolyzable radical (Y) is methoxy and the halogen (X) is chlorine. Particularly preferred are the following compounds:
N-(trimethoxysilylmethyl)octadecyldimethylammonium chloride,
N-(3-trimethoxysilylpropyl)hexadecyldimethylammonium chloride,
N-(6-trimethoxysilylhexyl)tetradecyldimethylammonium chloride,
N-(3-trimethoxysilylpropyl)tetradecyldimethylammonium chloride,
N-(5-trimethoxysilylpentyl)hexadecyldimethylammonium chloride,
N-(5-trimethoxysilylpentyl)tetradecyldimethylammonium chloride,
N-(6-trimethoxysilylhexyl)pentadecyldimethylammonium chloride,
N-(6trimethoxysilylhexyl)octadecyldimethylammonium chloride, and
N-(5-trimethoxysilylpentyl)octadecyldimethylammonium chloride.

Among these compounds, quite particularly preferred is N-(trimethoxysilylmethyl)octadecyldimethylammonium chloride.

The organosilicon quaternary ammonium compounds of formula I can be prepared in a conventional and well known manner, utilizing the procedures that are geneally described in U.S. Pat. Nos. 3,560,385 and 3,730,701. In this regard, the compounds of formula I can be suitably synthesized by heating at reflux temperature, in a polar solvent such as methanol, ethanol or acetone, an amine of the formula:

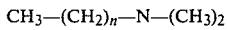

$$CH_3-(CH_2)_n-N-(CH_3)_2 \qquad III$$

wherein n is as above; with a silane of the formula:

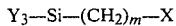

$$Y_3-Si-(CH_2)_m-X \qquad IV$$

wherein X, Y and m are as above.

The compounds of formula I have significant antimicrobial activity. For this reason, the compounds are useful for the control of gram-positive and gram-negative bacteria, algae, yeast, fungi and other microorganisms.

Aqueous or alcoholic solutions of the compounds of formula I can be used to treat textiles, minerals, glass and many other substrates, to render the surfaces of the substrates resistant to the growth of microorganisms. Preferably, the substrates treated with a compound of formula I have free hydroxy groups on their surfaces. In this regard, it has been found that, after treatment of a substrate surface, having free hydroxy groups, with an alcohol solution of a compound of formula I, the compound is not readily washed off or leached from the treated substrate surface by water. It is believed that this phenomenon results from the formation of covalent bonds between the silyl moiety of the compound of formula I and the free hydroxy groups on the surface of the substrate, whereby the compound of formula I is chemically bonded to the substrate's surface.

Any substrate having free hydroxy groups on its surface can be usefully treated with a compound of formula I. Among the substrates having free hydroxy groups on their surfaces, which can be suitably bonded to the compounds of formula I, are natural and manmade fiber fabrics, such as cotton, wool, linen, felt, acrylic, polyester, cellulose acetate, rayon, nylon and vinyl, and metals such as aluminum, stainless steel and galvanized metal, as well as wood, rubber, paper, glass and ceramic.

Of course, substrates having no free hydroxy groups on their surfaces, such as silicone polymers, also can be treated with the compounds of formula I to render them resistant, at least temporarily, to microorganisms. This can be accomlished by spraying, dipping or otherwise applying the compounds of formula I to such substrates, so that the compounds adhere for a while to the substrates' surfaces. Preferably, substrates, such as plastics, rubbers, paints, ointments, and fabrics, which do not have free hydroxy groups on their surfaces are made resistant to the growth of microorganisms by adding a compound of formula I to powdered or liquid materials, such as solid or liquid silicon polymers, which are subsequently formed into the substrates.

The treatment of a substrate with a compound of formula I, to render the substrate's surface resistant to the growth of microorganisms, can be suitably carried out in a simple manner, particularly if the substrate's surface has free hydroxy groups, so that the compound cannot be readily washed off or leached from the substrate after it has been applied to the substrate. For example, a compound of formula I can generally be applied satisfactorily to a substrate, using the techniques known for applying N-(3-trimethoxysilyl)propyldimethyloctadecylammonium chloride to the substrate, e.g., by simply immersing the substrate in an aqueous or alcoholic solution of the compound, so that an effective amount of the compound adheres to all of the substrate's surface, without significant areas of the substrate being uncovered.

The quantity of the compound of formula I which is required to render a substrate resistant to a particular microorganism will generally vary, depending upon the particular kind of microorganism, the particular compound, and the specific substrate. However, the concentration of the compound of formula I in an aqueous or alcoholic, treating solution, in which a substrate is to be dipped, and the immersion time are generally not critical. In this regard 1,000 to 10,000 ppm of a compound of formula I in the treating solution are generally sufficient, although in some cases up to 100,000 ppm of the compound may be required in the solution. Also, immersion times of 1 to 60 minutes are generally sufficient, although immersion times of only about 5 to 10 minutes are frequently preferred.

The Example which follows further illustrates this invention. In the Example, the following organosilicon quaternary ammonium compounds were tested:

A. N-(trimethoxysilylmethyl)octadecyldimethylammonium chloride
B. N-(3-trimethoxysilylpropyl)hexadecyldimethylammonium chloride
C. N-(6-trimethoxysilylhexyl)tetradecyldimethylammonium chloride
D. N-(3-trimethoxysilylpropyl)tetradecyldimethylammonium chloride
E. N-(5-trimethoxysilylpentyl)hexadecyldimethylammonium chloride
F. N-(5-trimethoxysilylpentyl)tetradecyldimethylammonium chloride
G. N-(6-trimethoxysilylhexyl)pentadecyldimethylammonium chloride
H. N-(11-trimethoxysilylundecyl)decyldimethylammonium chloride
I. N-(4-trimethoxysilylbutyl)tetradecyldimethylammonium chloride
J. N-(6-trimethoxysilylhexyl)octadecyldimethylammonium chloride
K. N-(4-trimethoxysilylbutyl)octadecyldimethylammonium chloride
L. N-(5-trimethoxysilylpentyl)octadecyldimethylammonium chloride
M. N-(4-trimethoxysilylbutyl)heptadecyldimethylammonium chloride
N. N-(3-trimethoxysilylpropyl)octadecyldimethylammonium chloride [Prior Art].

EXAMPLE

Treated and control sheets of Whatman no. 1 filter paper were cut into 2 inches by 1/4 inch strips. Each strip was placed in a capped test tube and sterilized with ethylene oxide. Each strip was then inoculated with $10^7$–$10^8$ colony-forming units of *Staphylococcus aureus*. This inoculum was experimentally determined to be the least number of colony-forming units of the microorganism which would consistently yield positive results after incubation for one, three and six days. k The inoculated strips were incubated at room temperature (about 23° C.) for either one (1), three (3) or six (6) days. Following incubation, 10 ml of nutrient broth were added to each test tube containing one of the three types of inoculated strips of filter paper. Then, the tubes were incubated for another 48 hours at 35° C. and thereafter observed for turbidity, indicative of bacterial growth.

Each treated strip of Whatman no. 1 filter paper, used in the Example, was prepared by saturating a web of the filter paper with a methanolic solution of one of the organosilicon quaternary ammonium compounds (A to N), being tested, in a conventional laboratory saturator at room temperature. After being saturated with a solution of one of the compounds, each treated web was air dried and then cut into strips.

The methonolic solutions of the compound (A to N), used to treat the webs of Whatman filter paper, were each prepared by: initially dissolving one of the compounds in methanol, so that the methanolic solution comprised 5-15% (by weight) of the compound and 85-95% methanol; and then diluting the methanolic solution with water so that there were 1 to 10 millimoles (mM) of the compound per liter of the aqueous methanolic solution.

The comparisons of bacterial growth on the treated paper strips versus the control paper strips, for the three types of inoculated paper strips, are summarized in Tables 1, 2 and 3 which follow. Treatment of each paper strip in Table 1 was with a 1.0 mM solution of one of the compounds, treatment of each paper strip in Table 2 was with a 5.0 mM solution of one of the compounds, and treatment of each paper strip in Table 3 as with a 10.0 mM solution of one of the compounds.

As seen from the data in Tables 1 to 3, all of the compounds of formula I (Compounds A to M) demonstrated greater antimicrobial activity than N-(3-trimethoxysilylpropyl)octadecyldimethylammonium chloride (compound N) in at least 6 of the 9 tests conducted.

TABLE 1

Comparison of Antimicrobial Activity of Compounds Saturated on Whatman Filter Paper from a 1.0 mM solution Ratio of Positive Cultures on Treated Paper to Positive Cultures on Control Paper

| Compound | Day 1 | Day 3 | Day 6 |
|---|---|---|---|
| A | 0 (0/30) | 0 (0/30) | 0 (0/30) |
| D | 0.17 (10/59) | 0.03 (2/59) | 0 (0/59) |
| B | 0.15 (9/60) | 0.08 (5/60) | 0 (0/59) |
| E | 0.10 (6/60) | 0.08 (5/60) | 0.02 (1/60) |
| G | 0.20 (6/30) | 0.13 (4/30) | 0 (0/30) |
| C | 0.25 (5/20) | 0 (0/30) | 0.05 (1/20) |
| F | 0.52 (31/60) | 0.20 (12/60) | 0.02 (1/60) |
| J | 0.37 (22/60) | 0.22 (13/60) | 0.15 (9/60) |
| I | 0.60 (24/40) | 0.30 (12/40) | 0.05 (2/39) |
| K | 0.54 (27/50) | 0.40 (20/50) | 0.06 (3/49) |
| M | 0.65 (26/40) | 0.38 (15/40) | 0.13 (5/39) |
| L | 0.50 (30/60) | 0.40 (24/60) | 0.22 (13/60) |
| N [Prior Art] | 0.68 (82/120) | 0.48 (53/110) | 0.34 (37/110) |
| H | 0.83 (33/40) | 0.48 (19/40) | 0.30 (12/40) |

TABLE 2

Comparison of Antimicrobial Activity of Compounds Saturated on Whatman Filter Paper from a 5.0 mM Solution Ratio of Positive Cultures on Treated Paper to Positive Cultures on Control Paper

| Compound | Day 1 | Day 3 | Day 6 |
|---|---|---|---|
| A | 0 (0/50) | 0 (0/50) | 0 (0/43) |
| C | 0 (0/20) | 0 (0/20) | 0 (0/20) |
| F | 0.03 (2/60) | 0 (0/60) | 0 (0/60) |
| B | 0.03 (2/60) | 0.02 (1/60) | 0 (0/59) |
| D | 0.08 (5/59) | 0.02 (1/59) | 0 (0/59) |
| I | 0.10 (4/40) | 0.03 (1/40) | 0 (0/39) |
| J | 0.13 (10/80) | 0.06 (5/79) | 0.03 (2/80) |
| H | 0.54 (27/50) | 0.08 (4/50) | 0 (0/43) |
| G | 0 (0/50) | 0.18 (9/50) | 0.07 (3/43) |
| L | 0.23 (21/90) | 0.10 (9/89) | 0.05 4/83 |
| K | 0.26 (18/70) | 0.14 (10/69) | 0.04 (3/69) |
| E | 0.13 (10/80) | 0.14 (11/80) | 0.11 (8/73) |
| M | 0.33 (20/60) | 0.32 (19/60) | 0.20 (10/50) |
| N [Prior Art] | 0.56 (84/150) | 0.31 (46/149) | 0.20 (29/142) |

TABLE 3

Comparison of Antimicrobial Activity of Compounds Saturated on Whatman Filter Paper from a 10.0 mM Solution Ratio of Positive Cultures on Treated Paper to Positive Cultures on Control Paper

| Compound | Day 1 | Day 3 | Day 6 |
|---|---|---|---|
| A | 0 (0/50) | 0 (0/50) | 0 (0/43) |
| E | 0 (0/50) | 0 (0/50) | 0 (0/43) |
| H | 0 (0/30) | 0 (0/30) | 0 (0/23) |
| G | 0 (0/20) | 0 0/20 | 0 (0/13) |
| B | 0 (0/60) | 0 (0/60) | 0 (0/59) |
| F | 0 (0/60) | 0 (0/60) | 0 (0/60) |
| C | 0 (0/20) | 0 (0/20) | 0 (0/20) |
| D | 0.017 (1/59) | 0 (0/59) | 0 (0/59) |
| M | 0 (0/30) | 0.100 (3/30) | 0 (0/21) |
| I | 0 (0/40) | 0 (0/40) | 0.154 (6/39) |
| K | 0 (0/70) | 0.145 (10/69) | 0 (0/69) |
| J | 0 0/80 | 0.025 (2/79) | 0.013 (1/80) |
| L | 0.113 (2/80) | 0.013 (1/79) | 0 (0/73) |
| N [Prior Art] | 0.125 (15/120) | 0.034 (4/119) | 0.018 (2/113) |

I claim:

1. A compound of the formula:

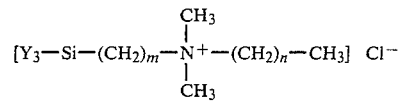

wherein m+n is 16 to 19, m is 1 or 4 to 6 and n is 13 to 17 or m+n is 20 to 23, m is 4 to 11 and n is 9 to 17; and Y is a hydrolyzable radical or hydroxy group.

2. The compound of claim 1, selected from the group consisting of:
N-(trimethoxysilylmethyl)octadecyldimethylammonium chloride,
N-(6-trimethoxysilylhexyl)tetradecyldimethylammonium chloride,
N-(5-trimethoxysilylpentyl)hexadecyldimethylammonium chloride,
N-(5-trimethoxysilylpentyl)tetradecyldimethylammonium chloride,
N-(6-trimethoxysilylhexyl)pentadecyldimethylammonium chloride,
N-(6-trimethoxysilylhexyl)octadecyldimethylammonium chloride, and
N-(5-trimethoxysilylpentyl)octadecyldimethylammonium chloride.

3. The compound of claim 1 which is N-(trimethoxysilylmethyl)octadecyldimethylammonium chloride.

* * * * *

UNITED STATES PATENT AND TRADEMARK OFFICE
CERTIFICATE OF CORRECTION

PATENT NO. : 4,282,366
DATED : August 4, 1981
INVENTOR(S) : William Wayne Eudy

It is certified that error appears in the above—identified patent and that said Letters Patent is hereby corrected as shown below:

Col. 2, line 34 - "2," (first occurrence) should be -- 2' --;

Col. 2, line 62 - "6" should be -- 6- --;

Col. 3, line 4 - "geneally" should be -- generally --

Col. 4, line 68 - Delete "K"

Col. 5, line 37 - "as" should be -- was --.

Signed and Sealed this

Thirtieth Day of March 1982

[SEAL]

Attest:

Attesting Officer

GERALD J. MOSSINGHOFF

*Commissioner of Patents and Trademarks*